United States Patent [19]

Gillis

[11] Patent Number: 5,222,969
[45] Date of Patent: Jun. 29, 1993

[54] INTRAVASCULAR STENT FOR CARDIOVASCULAR INTERVENTION

[76] Inventor: Rolando Gillis, 12908 SW. 48 Street, Miami, Fla. 33175

[21] Appl. No.: 851,760

[22] Filed: Mar. 16, 1992

[51] Int. Cl.⁵ .............................................. A61M 29/00
[52] U.S. Cl. ...................................... 606/194; 604/96
[58] Field of Search .............. 623/1; 604/96; 606/191, 606/192, 194, 195, 200

[56] References Cited

U.S. PATENT DOCUMENTS

| | | | |
|---|---|---|---|
| 5,037,427 | 8/1991 | Harada et al. | 604/96 |
| 5,127,917 | 7/1992 | Neiderhauser et al. | 604/96 |

OTHER PUBLICATIONS

Chapters 26 and 27, Coronary Angioplasty. Baim and New Devices for Coronary Intervention: Intravascular Stents and Coronary Atherectomy Catheters, Safian et al., Lea and Febrigley, 200 Chester Field Parkway, Philadelphia, Pa. pp. 441-491, 1991.

*Primary Examiner*—Jerome L. Kruter
*Attorney, Agent, or Firm*—Malloy & Malloy

[57] ABSTRACT

A coil spring shaped stent to reinforce an arterial wall, along a length thereof, where plaque has been removed by a balloon catheter; the stent is of a wire of a suitable material, such as stainless steel or gold, which is sized and configured to define spaced coils; the wire has axially spaced, enlarged bearing portions and a roller between each of the bearing portions to facilitate advancement and withdrawal of the coil spring shaped stent upon final positioning in an artery.

3 Claims, 1 Drawing Sheet

INTRAVASCULAR STENT FOR CARDIOVASCULAR INTERVENTION

SUMMARY OF THE INVENTION

This invention relates to an intravascular stent for use in cardiovascular intervention.

BACKGROUND OF THE INVENTION

It is well-known that to remove plaque from an artery, a balloon on the tip of a catheter may be positioned where the artery is constricted; and thereafter, the balloon is expanded, which breaks the plaque free, reducing the constriction. The problem has been that this weakens the arterial wall where the balloon has been expanded. It is known in the art to provide a tubular stent at that location to reinforce the artery, the stent remaining in the artery when the operation is completed. One of the problems is the proper location of the stent which will remain in the artery. In order to ensure that the proper location is achieved, x-ray technology is utilized which requires the stent be visible with x-rays. The axial location of the stent is important and axial adjustment of advancement or withdrawal is often required. There have been problems in the past with achieving sufficient visibility and of making final axial adjustment. This invention is of an improved stent which is highly "visible" and which can be readily adjusted axially.

Generally speaking, in a cardiovascular intervention, a catheter having an expandable balloon-type tip is inserted into the artery; and the balloon is expanded when in position at a constricted zone. A tubular catheter is then used to advance a stent along the balloon tipped cather to reinforce the expanded zone. In this invention, between the balloon tip and the distal end of the catheter jacketing the balloon tipped catheter, a stent is provided. It is a generally tubular reinforcement member of a coil spring shape which is provided with rollers to facilitate axial adjustment.

In this invention, the coil shaped stent is provided with a diameter slightly greater than the diameter of the distal end of a tubular catheter jacketing the balloon catheter; and the stent is also of a diameter slightly less than the diameter of the expanded balloon. Thus, when the tubular jacketing catheter or push catheter is advanced, it will bear against the proximal end of the stent and force it in a forward axial direction. To adjust the stent, when a degree of withdrawal is required, the balloon, when expanded, bears against the distal stent end to pull it rearwardly when the balloon catheter is withdrawn somewhat.

In operation, generally speaking, the balloon tip catheter is advanced to the site of the plaque and, there, expanded to free the plaque. The stent is then required to be located where the balloon was expanded. In order to do this, a tubular catheter jacketing the balloon catheter is advanced pushing the stent advancing it along the exterior of the balloon tipped catheter. The location of the stent can then be checked to be sure it is in the correct location using x-rays. If advancement is required, the jacketing catheter is advanced which pushes the stent along the balloon tipped catheter to the correct axially location. On the other hand, if the stent must be withdrawn slightly, the balloon tip is expanded and the balloon tipped catheter is withdrawn slightly pulling the stent axially rearwardly to the correct location. There the stent remains in situ to reinforce the arterial wall. When the stent is properly located, the balloon is collapsed and withdrawn through the stent and removed together with the jacketing tubular catheter.

It is an object of this invention to provide an improved stent which is in the shape of a coil spring of a uniform diameter, formed from a wire along which there are spaced bearings with a roller between adjacent bearings. The spring and rollers are preferably of a suitable metallic material, such as gold or stainless steel.

DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DESCRIPTION OF THE PREFERRED EMBODIMENT

Figure 1:
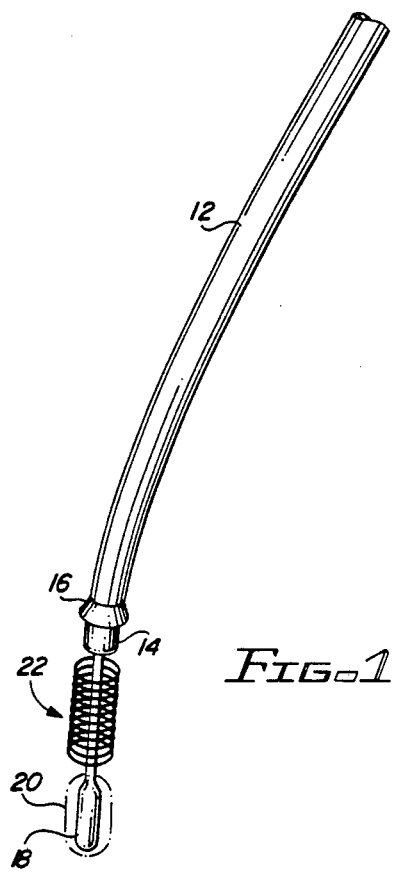
FIG. 1 is a view of the end of the push catheter, balloon catheter with the stent captivated between the balloon catheter and the push catheter, the balloon being expanded.

Referring to the drawings, there is shown a tubular catheter 12 which has a distal end 14 adjacent to which, preferably, there is an enlarged portion. Extending coaxially through this tubular catheter 12, there is a balloon tipped catheter generally designed by the numeral 18. The balloon when collapsed is of a smaller diameter then the inside diameter of the tubular catheter. However, when expanded as shown by the dotted lines at 20, it is of a larger diameter than the inside diameter of the distal tip of the jacketing catheter 12. In use, the balloon tip catheter 18 is advanced so that the balloon is at the site of a plaque build-up. While there located, the balloon is expanded to free the plaque at that location. Thereafter, a stent is advanced to the location at which the balloon is to be found. It is advanced by axially pushing it so that the distal end of the jacketing catheter 14 pushes the stent. The stent designated by the numeral 22 is of a diameter somewhat greater than the inside diameter of the catheter and of a diameter slightly less than the diameter of the expanded balloon. When the stent has been advanced to a point adjacent the location of the expanded balloon, it is then further advanced so that the stent occupies the site at which the expansion of the balloon took place. Thereafter, the balloon is collapsed and the balloon tip catheter may be withdrawn through the push catheter 12 and the two catheters removed from the artery, while the stent remains at the location in which the plaque was broken away. There the stent reinforces the artery wall and preventing its subsequent collapse of it resulting from the weakening which customarily and often takes place when the artery has been expanded.

The problems in the prior art have been one the x-ray visibility of stents, that is seeing that the stent by the use of x-rays to locate it properly and of final axial movement to the correct position in the artery. This invention provides a stent of stainless steel or other suitable material such as gold which is readily visible with x-rays.

Figure 2:
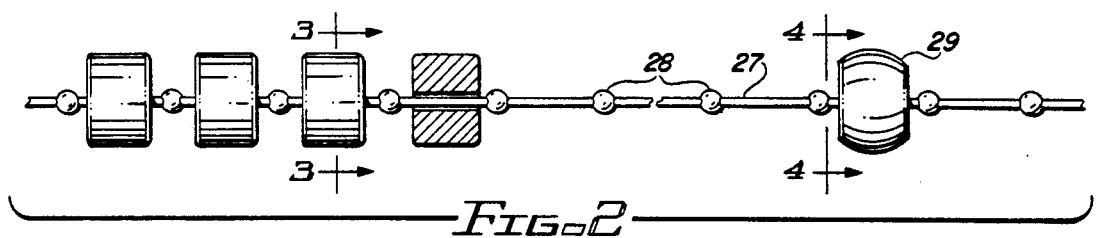
FIG. 2 is a view of a wire with bearings and rollers arranged thereon.
Figure 5:
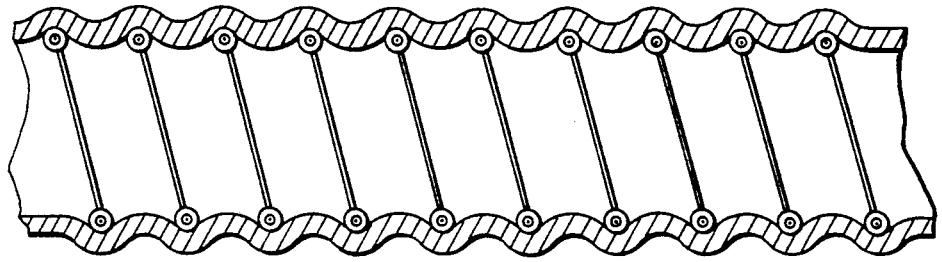
FIG. 5 is a partial view of one surface of the stent when inserted and positioned in an arterial wall and illustrating the arterial wall relative to the stent surface.

The axial adjustment means of the stent will now be described. Referring more particularly to the stent 20, seen in FIG. 2, it is seen that it is of a coil spring structure of a predetermined axial length formed from a wire 27. Along the length of the coil wire, there are spaced enlarged diameter portions referred to as bearings 28. Captivated between each of the bearings enlarged diameter portions 28, there is provided a bead or roller 29. Thus, the entire surface of the spring is composed of spaced rollers, the rollers being held in spaced relation and out of engagement of one roller with the adjacent roller by the enlarged portions 26. The stent is relatively strong so as to resist axial forces tending to collapse it when being inserted. This is so that the coils of the spring are not forced one against the other which would jam the action of the rollers. In short, the coil spring shape is not intended to collapse in an axial direction but is intended to remain in its form and configuration so that the rollers are free to move and assist in the advancement or withdrawal of the spring carrying the rollers. Once in the place as the arterial wall 31 tends to collapse, it assumes a somewhat corrugated shape resisting axial movement of displacement.

Thus, this invention is of an improved intravascular stent for use with a balloon tipped catheter for coronary intervention. It is characterized by a coil spring shape formed from a wire and being of a predetermined axial length. Along the wire closely adjacent spaced enlarged bearing portions are provided with a roller captivated between each of the bearing portions to assist in the ease of advancement or withdrawal of the stent by pushing upon the stent ends with either the catheter jacketing the balloon tip or pulling it by the expanded balloon tip.

Figure 3:
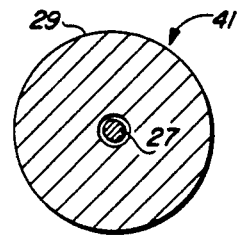
FIG. 3 is a view in cross-section of one type of roller.
Figure 4:
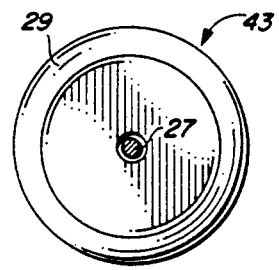
FIG. 4 is a somewhat modified form of roller.

As seen in FIG. 3, the rollers may be cylindrically shaped as at 41 or, alternatively, their respective surfaces may be somewhat oval-shaped as shown in FIG. 4 in which the roller is designated by the numeral 43.

While this invention has been shown and described in what is considered to be a practical and preferring embodiment, it should be recognized that departures may be made within the spirit and scope of this invention within the doctrine of equivalents.

What is claimed is:

1. A stent means of coil spring configuration and predetermined axial length to be used in cardiovascular intervention by axial insertion and position adjustment axially in an artery to reinforce the wall of an artery where plaque has been freed to maintain the arterial wall about the cross-sectional area of the artery from closure by collapse of the artery wall, said stent means, when being inserted in an artery being positioned in circumposed relation about the distal end zone of a balloon tipped catheter having a distally located expandable balloon portion, the balloon portion having a predetermined expanded maximum diameter, said stent means being sized and configured to be captivated, upon position adjustment axially between a) the balloon portion when expanded, and b) the distal end of a tubular push catheter in circumposed relation about the balloon tipped catheter, the push catheter having a distal end of a predetermined inside diameter, said stent means having a generally uniform diameter less than the predetermined expanded maximum diameter of the balloon tip and greater than the predetermined inside diameter of said push catheter distal end, said stent means comprising a coiled wire defining coils and having strength characteristics such that it does not collapse axially upon being pushed by the distal end of the tubular push catheter, the coils of said stent means being spaced axially from one another a first predetermined distance, and said wire including axially spaced diametrically enlarged bearing portions; and a roller means captivated between each enlarged bearing portion to facilitate advancement and withdrawal of the stent means, and said roller means of adjacent coils having closely adjacent axially facing surfaces, the outside diameter of said stent means being slightly greater than the cross-sectional area of the space to be reinforced in the arterial wall by said stent means.

2. The stent means as set forth in claim 1 wherein the stent means is of stainless steel material.

3. The stent means as set forth in claim 1 wherein the stent means is of gold.

* * * * *